United States Patent
Av-Gay et al.

(10) Patent No.: US 9,814,623 B2
(45) Date of Patent: Nov. 14, 2017

(54) ANTIMICROBIAL GAS IMPREGNATING DEVICES AND METHODS

(75) Inventors: Yossef Av-Gay, Vancouver (CA); David Greenberg, Vancouver (CA)

(73) Assignee: ENOX (ISRAEL) LTD., Tel Aviv (IL)

( * ) Notice: Subject to any disclaimer, the term of this patent is extended or adjusted under 35 U.S.C. 154(b) by 28 days.

(21) Appl. No.: 12/825,373

(22) Filed: Jun. 29, 2010

(65) Prior Publication Data

US 2010/0268149 A1    Oct. 21, 2010

Related U.S. Application Data

(63) Continuation of application No. 12/234,599, filed on Sep. 19, 2008.

(60) Provisional application No. 60/974,228, filed on Sep. 21, 2007.

(51) Int. Cl.
| | | |
|---|---|---|
| *A61F 11/00* | (2006.01) | |
| *A61M 27/00* | (2006.01) | |
| *A61K 33/00* | (2006.01) | |
| *A61L 31/04* | (2006.01) | |
| *A61L 31/10* | (2006.01) | |
| *A61L 31/16* | (2006.01) | |

(52) U.S. Cl.
CPC .......... *A61F 11/002* (2013.01); *A61K 33/00* (2013.01); *A61L 31/04* (2013.01); *A61L 31/10* (2013.01); *A61L 31/16* (2013.01); *A61M 27/002* (2013.01); *A61L 2300/114* (2013.01); *A61L 2300/404* (2013.01); *A61L 2300/45* (2013.01); *A61L 2430/14* (2013.01)

(58) Field of Classification Search
CPC ......... A61M 27/002; A61M 2210/0662; A61L 2300/114; A61L 2300/404; A61L 2430/14
See application file for complete search history.

(56) References Cited

U.S. PATENT DOCUMENTS

| | | |
|---|---|---|
| 4,417,576 A | 11/1983 | Baran |
| 4,592,920 A | 6/1986 | Murtfeldt |
| 4,603,152 A | 7/1986 | Laurin et al. |

(Continued)

FOREIGN PATENT DOCUMENTS

| | | |
|---|---|---|
| EP | 2195042 | 6/2010 |
| WO | WO 96/20019 | 7/1996 |

(Continued)

OTHER PUBLICATIONS

International Preliminary Report on Patentability dated Apr. 1, 2010 From the International Bureau of WIPO Re. Application No. PCT/CA2008/001658.

(Continued)

*Primary Examiner* — Andrew Gilbert
(74) *Attorney, Agent, or Firm* — Browdy and Neimark, PLLC

(57) ABSTRACT

A nitric oxide gas-releasing conduit configured for surgical implantation through a patient's tympanic membrane. The nitric oxide gas-releasing conduit comprises a gas-permeable cured resin material configured for releasably sequestering therein gas. The gas-permeable cured resin material is charged with nitric oxide gas. The nitric oxide gas-releasing conduit may be optionally coated with an antimicrobial gas-releasing composition. The gas-releasing coating composition may be configured to release nitric oxide.

8 Claims, 7 Drawing Sheets

(56) References Cited

U.S. PATENT DOCUMENTS

| | | | |
|---|---|---|---|
| 4,677,143 A | 6/1987 | Laurin et al. | |
| 5,049,140 A | 9/1991 | Brenner et al. | |
| 5,417,657 A | 5/1995 | Hauer | |
| 5,505,695 A | 4/1996 | Eplett, Jr. | |
| 5,525,357 A | 6/1996 | Keefer et al. | |
| 5,535,357 A * | 7/1996 | Moran et al. | 711/103 |
| 5,820,917 A * | 10/1998 | Tuch | A61L 27/34 427/2.1 |
| 5,857,998 A | 1/1999 | Barry | |
| 6,361,526 B1 * | 3/2002 | Reisdorf et al. | 604/265 |
| 6,425,881 B1 | 7/2002 | Kaesemeyer | |
| 6,494,314 B1 | 12/2002 | Lamborne et al. | |
| 6,494,862 B1 | 12/2002 | Ray et al. | |
| 6,656,506 B1 | 12/2003 | Wu et al. | |
| 6,689,302 B2 | 2/2004 | Reisdorf et al. | |
| 6,841,166 B1 | 1/2005 | Zhang et al. | |
| 8,043,246 B2 | 10/2011 | Av-Gay et al. | |
| 8,282,967 B2 * | 10/2012 | Schoenfisch et al. | 424/718 |
| 2002/0095114 A1 | 7/2002 | Palasis | |
| 2003/0039697 A1 | 2/2003 | Zhao et al. | |
| 2003/0114793 A1 | 6/2003 | Freyman | |
| 2004/0247640 A1 * | 12/2004 | Zhao et al. | 424/423 |
| 2005/0063859 A1 | 3/2005 | Masuda et al. | |
| 2007/0207186 A1 * | 9/2007 | Scanlon et al. | 424/424 |
| 2008/0038354 A1 * | 2/2008 | Slager et al. | 424/487 |
| 2008/0160064 A1 * | 7/2008 | Capelli et al. | 424/423 |
| 2009/0131883 A1 | 5/2009 | Av-Gay et al. | |
| 2009/0255536 A1 * | 10/2009 | Av-Gay et al. | 128/207.14 |
| 2011/0076313 A1 | 3/2011 | Av-Gay et al. | |
| 2011/0106000 A1 * | 5/2011 | Jones et al. | 604/23 |

FOREIGN PATENT DOCUMENTS

| | | | |
|---|---|---|---|
| WO | WO 02/056864 | | 7/2002 |
| WO | WO 03/032928 | | 4/2003 |
| WO | WO-2006/078786 A1 * | | 1/2006 |
| WO | WO 2006/078786 | | 7/2006 |
| WO | WO/US2006/001847 | * | 7/2006 |
| WO | WO 2006/084910 | | 8/2006 |
| WO | WO 2007/028657 | | 3/2007 |
| WO | WO 2009/036571 | | 3/2009 |

OTHER PUBLICATIONS

International Search Report dated Jan. 6, 2010 From the International Searching Authority Re. Application No. PCT/CA2008/001658.
Supplementary European Search Report and the European Search Opinion dated Aug. 4, 2010 From the European Patent Office Re. Application No. 08800359.5.
Written Opinion dated Jan. 6, 2009 From the International Searching Authority Re. Application No. PCT/CA2008/001658.
Official Action dated Mar. 10, 2010 From the US Patent and Trademark Office Re. U.S. Appl. No. 12/234,599.
Official Action dated Jun. 26, 2009 From the US Patent and Trademark Office Re. U.S. Appl. No. 12/234,599.
Official Action dated Oct. 26, 2010 From the US Patent and Trademark Office Re. U.S. Appl. No. 12/234,599.
Official Action dated Aug. 31, 2010 From the US Patent and Trademark Office Re. U.S. Appl. No. 12/234,599.
Response Dated Nov. 6, 2009 to Official Action dated Jun. 26, 2009 From the US Patent and Trademark Office Re. U.S. Appl. No. 12/234,599.
Response Dated Jun. 10, 2010 to Official Action dated Mar. 10, 2010 From the US Patent and Trademark Office Re. U.S. Appl. No. 12/234,599.
Response Dated Nov. 30, 2010 to Official Action dated Aug. 31, 2010 From the US Patent and Trademark Office Re. U.S. Appl. No. 12/234,599.
Translation of Notification of Reasons for Refusal dated Jun. 1, 2010 From the Japanese Patent Office Re. Application No. 2006-545287.
Baker et al. "A Randomized Clinical Trial of Topical Gentamicin After Tympanostomy Tube Placement", Archives of Otolaryngology—Head & Neck Surgery, 114(7): 755-757, Jul. 1988.
Balkany et al. "A Prospective Study of Infection Following Tympanostomy and Tube Insertion", the American Journal of Otology, 4(4): 288-291, Apr. 1983.
Birck et al. "Myringostomy for Middle Ear Effusions. Results of a Two-Year Study", The Annals of Otology, Rhinology and Laryngology, 85(2 Suppl.25 Pt.2): 263-267, Mar.-Apr. 1979.
Gates et al. "Post-Tympanostomy Otorrhea", Laryngoscope, 96: 630-634, Jun. 1986.
Ghaffari et al. "Potential Application of Gaseous Nitric Oxide as a Topical Antimicrobial Agent", Nitric Oxide, 14: 21-29, 2006.
McMullin et al. "The Antimicrobial Effect of Nitric Oxide on the Bacteria That Cause Nosocomial Pneumonia in Mechanically Ventilated Patients in the Intensive Care Unit", Respiratory Care, 50(11): 1451-1456, 2005.
Communication Pursuant to Rules 70(2) and 70a(2) EPC dated Aug. 23, 2010 From the European Patent Office Re. Application No. 08800359.5.
Response Dated Feb. 23, 2011 to Communication Pursuant to Rules 70(2) and 70a(2) EPC dated Aug. 23, 2010 From the European Patent Office Re. Application No. 08800359.5.
Baker, R.S., et al., "A Randomized Clinical Trial of Topical Gentamicia After Tympanostomy Tube Placement" ,Arc. Otolaryngology Head and Neck Surgery, vol. 114, 1998, pp. 755-757.
Balkany et al., "A Prospective Study of Infection Following Tympanostomy and Tube Insertion," American Journal of Otology, vol. 4, 1983, pp. 288-291.
Birck, H.G., et al., "Myringotomy for Middle Ear Effusions", Ann. of Otol. Rhino. Laryngo, vol. 85, 1979, pp. 263-267.
Gates, G.A., et al., "Post Tympanostomy Otorrhea", Laryngoscope, vol. 96, 1986, pp. 630-634.
Ghaffari, et al., Nitric Oxide, vol. 14, 2005, pp. 21-29.
Machine Design, May 23, 1967, p. 192.
McMullin et al., Respir. Care, vol. 5, pp. 1451-1456.
Packaging Encyclopedia, vol. 33, No. 5, 1988, pp. 54-55.
Translation of Office Action and Search Report dated Aug. 31, 2012 From the State Intellectual Property Office of the People's Republic of China Re. Application No. 200880113177.5.
Requisition by the Examiner and the Examination Search Report dated Dec. 2, 2014 From the Canadian Intellectual Property Office Re. Application No. 2,700,172.
Notice of Grounds for Rejection dated Sep. 2, 2014 From the Korean Intellectual Property Office Re. Application No. 10-2010-700806063 and Its Translation Into English.
Official Action dated Apr. 9, 2014 From the US Patent and Trademark Office Re. U.S. Appl. No. 12/825,370.
Restriction Official Action dated May 23, 2012 From the US Patent and Trademark Office Re. U.S. Appl. No. 12/825,370.
Examination Report dated May 29, 2013 From the Instituto Mexicana de la Propiedad Industrial Re. Application No. MX/a/2010/003087 and Its Summary in English.
Official Action dated Mar. 17, 2015 From the US Patent and Trademark Office Re. U.S. Appl. No. 12/825,370.
Requisition by the Examiner dated Sep. 23, 2015 From the Canadian Intellectual Property Office Re. Application No. 2,700,172.
Official Action dated Jun. 18, 2015 From the US Patent and Trademark Office Re. U.S. Appl. No. 12/825,370.
Official Action dated Dec. 7, 2015 From the US Patent and Trademark Office Re. U.S. Appl. No. 12/825,370.
Official Action dated Apr. 19, 2016 From the US Patent and Trademark Office Re. U.S. Appl. No. 12/825,370.
Applicant-Initiated Interview Summary dated Feb. 15, 2017 From the US Patent and Trademark Office Re. U.S. Appl. No. 12/825,370. (4 pages).
Advisory Action Before the Filing of an Appeal Brief dated Mar. 31, 2017 From the US Patent and Trademark Office Re. U.S. Appl. No. 12/825,370. (9 pages).
Official Action dated Dec. 21, 2016 From the US Patent and Trademark Office Re. U.S. Appl. No. 12/825,370. (12 pages).
Notice of Allowance dated Jul. 11, 2011 From the US Patent and Trademark Office Re. U.S. Appl. No. 12/234,599.

(56) References Cited

OTHER PUBLICATIONS

Official Action dated Aug. 4, 2011 From the US Patent and Trademark Office Re. U.S. Appl. No. 12/825,370.
Response Dated Oct. 3, 2011 to Official Action dated Aug. 4, 2011 From the US Patent and Trademark Office Re. U.S. Appl. No. 12/825,370.
Notice of Allowance dated Jul. 11, 2011 From the U.S. Patent and Trademark Office Re. U.S. Appl. No. 12/234,599.
Communication Under Rule 71(3) EPC dated Apr. 20, 2012 From the European Patent Office Re. Application No. 08800359.5.
Communication Pursuant to Article 94(3) EPC Dated Sep. 27, 2011 From the European Patent Office Re. Application No. 08800359.5.
Response dated Oct. 3, 2011 to Official Action dated Aug. 4, 2011 From the U.S. Patent and Trademark Office Re. U.S. Appl. No. 12/825,370.
Response dated Nov. 24, 2011 to Communication Pursuant to Article 94(3) EPC dated Sep. 27, 2011 From the European Patent Office Re. Application No. 08800359.5.

* cited by examiner

ANTIMICROBIAL GAS IMPREGNATING DEVICES AND METHODS

CROSS-REFERENCE TO RELATED PATENT APPLICATIONS

This application is a divisional application of U.S. patent application Ser. No. 12/234,599, filed Sep. 19, 2008, now U.S. Pat. No. 8,043,246, which claims priority from U.S. Provisional Application No. 60/974,228, filed Sep. 21, 2007, all of which are incorporated herein by reference in their entirety.

BACKGROUND

Installation of tympanostomy tubes for the treatment of otitis media with effusion or in patients with recurrent events of acute otitis media, is a commonly performed surgical procedure in North America and elsewhere. In this procedure an incision is made in the tympanic membrane, fluid from within the middle ear is aspirated and a tympanostomy tube is inserted. The tubes can have various configurations and materials, and are effective in correcting the hearing loss due to the effusion as long as the tubes are in place in the ear. The materials which can be used to make tympanostoray tubes include thermoplastics such as modified elastomers and olefins, thermosets such as silicone and polytetrafluoroethylene; and metals such as stainless steel and titanium. Children with persistent middle ear effusions who do not respond to antibiotics undergo a procedure in which a myringotomy is performed in the tympanic membrane under local anesthesia. However the implantation of the tympanostomy tubes also be done under general anesthesia.

Purulent otorrhea frequently develops after tube insertion. In one study by H. G. Birck and J. J. Mravek "Myringotomy for Middle Ear Effusions," Ann. of Otol. Rhino. Laryngo., volume 85, pages 263-267 (1979), the investigators observed that 15% of children having tympanostomy tubes inserted in their ears following myringotomy developed postoperative otorrhea. In a more recent study by George A. Gates et al, "Post Tympanostomy Otorrhea," Laryngoscope, volume 96, pages 630-634, (June 1986), the investigators observed that the incidence of tympanostomy tube induced otorrhea following myringotomy was 18%. In a clinical study performed by Balkany et al, "A Prospective Study of Infection Following Tympanostomy and Tube Insertion," American Journal of Otology, volume 4, pages 288-291 (1983), the investigators observed an incidence of postoperative otorrhea of 19% in children receiving tympanostomy tubes with no antibiotic drops postoperatively applied. In the Balkany et al study, the investigators found that the incidence of postoperative otorrhea was reduced to 6% when antibiotic drops were put into the patient's ear after myringotomy. In another study on the use of antibiotics after myringotomy, R. S. Baker and R. A. Chole, "A Randomized Clinical Trial of Topical Gentamicia After Tympanostomy Tube Placement," Arch. Otolaryngology Head and Neck Surgery, volume 114, pages, 755-757 (July 1988), the investigators found that the incidence of infections in the experimental group using Gentamicin, an ophthalmic solution used as otic drops, had an incidence of infection significantly reduced by antibiotic drops.

In both the Balkany et al and Baker et al studies using antibiotic drops after tympanostomy, the investigators used potentially ototoxic antibiotics, namely Cortisporin and Gentamicin. Based on their frequency of use, and the lack of adverse effects noted in these studies, antibiotic drops are now used routinely to prevent postoperative otorrhea. However, thorough studies demonstrating the absence of adverse toxicological reaction in the use of antibiotic drugs for the treatment of postoperative otorrhea have not been published.

In addition to the relatively high incidence of otorrhea after myringotomy, investigators have observed children with implanted tympanostomy tubes sometimes experience bouts of otorrhea. Occasionally, the otorrhea became persistent causing some investigators to believe that the tympanostomy tubes become colonized with pathogenic bacteria.

The relatively high incidence of otorrhea after myringotomy and tympanostomy tube insertion exposes patients with persistent middle ear effusions to significant morbidity and additional treatment time and cost.

It would be desirable to utilize tympanostomy tubes whereby the incidence of otorrhea and other microbial induced infection after myringotomy and tympanostomy tube insertion could be substantially reduced without the use of antibiotics and the potential ototoxic reaction associated with the use of such drugs.

One approach for reducing bacterial infection encountered with the use of medical devices inserted into body cavities has been to apply an antimicrobial coating to the surface of the medical device. For example, U.S. Pat. No. 4,592,920 to Murtfeldt; U.S. Pat. No. 4,603,152 to Laurin et al and U.S. Pat. No. 4,677,143 to Laurin et al each teach applying a coating containing an antimicrobial agent such as silver oxide to the outer surfaces of medical devices such as catheters, enteral feeding tubes, endotracheal tubes and other hollow tubular devices.

U.S. Pat. No. 4,592,920 to Murtfeldt is primarily concerned with providing a surface coating of an antimicrobial metal compound on a medical device such as a catheter, but also discloses that the metal compound can be "imbedded" within the entire catheter. However, the Murtfeldt patent finds the imbedded construction to be less desirable since the antimicrobial metal compound imbedded within the side wall of the catheter has less likelihood of encountering migrating microbes and by inference is less effective than a surface coating.

U.S. Pat. No. 6,361,526 provides a tube formed from a thermoset resin containing therein between 0.5 to 15% by weight of a selected antimicrobial metal oxide compounds exemplified by silver oxide, that are capable of migrating to the sidewall surfaces of the tube. Such metal oxide-laden antimicrobial resin-based tubes are generally produced by controllably intermixing a selected metal oxide into a thermoset resin paste that is subsequently milled, then formed into a hollow tube by conventional tube-forming processes.

SUMMARY

In certain embodiments, ear drainage tubes are provided, including gas releasing antimicrobial ear drainage tubes. Exemplary embodiments of the present invention, are directed to antimicrobial gas-permeable gas-releasing conduits suitable for surgical implantation into and through patients' tympanic membranes. Suitable gas-permeable conduits are exemplified by tympanostomy tubes, myringotomy tubes and the like.

According to one aspect, the cured gas-permeable gas-releasing resin material comprises curable silicones.

According to another aspect, the antimicrobial gas-permeable gas-releasing molecules are exemplified by nitric oxide (NO) molecules.

According to another aspect the NO gas-permeable gas-releasing implantable conduits are coated with NO-releasing compositions exemplified by those having $N_2O_2^-$ functional groups, NO-releasing intramolecular salts, and S-nitrosothiols among others.

According to further aspect, the antimicrobial gas-permeable gas-releasing conduits are exemplified by tympanostomy tubes.

According to a further aspect, the antimicrobial gas-permeable gas-releasing conduits are exemplified by myringotomy tubes.

According to another exemplary embodiment of the present invention, the antimicrobial gas-permeable gas-releasing conduits are produced with a process whereby fully configured and cured gas-permeable resin-based tubes are controllably saturated with a selected antimicrobial gas exemplified by NO, whereby the resin-based tubes releasably sequester NO gas molecules. The antimicrobial gas-saturated conduits are individually packaged in gas-impermeable containers.

According to one aspect, the resin-based conduits sequestering therein NO gas molecules, are coated with NO-releasing compositions exemplified by those having $N_2O_2^-$ functional groups, NO-releasing intramolecular salts, and S-nitrosothiols among others.

According to a further embodiment, the antimicrobial gas-releasing conduits are produced by intermixing a suitable selected chelating agent saturated with antimicrobial gas molecules, with a curable polymeric resin material. The intermixed material is formed and configured into a plurality of antimicrobial gas-releasing conduits, then cured. After curing, the antimicrobial gas-releasing conduits are individually packaged and sealed into gas-impermeable containers.

BRIEF DESCRIPTION OF THE DRAWINGS

The present invention will be described in conjunction with reference to the following drawings, in which.

DETAILED DESCRIPTION

Figure 1A:
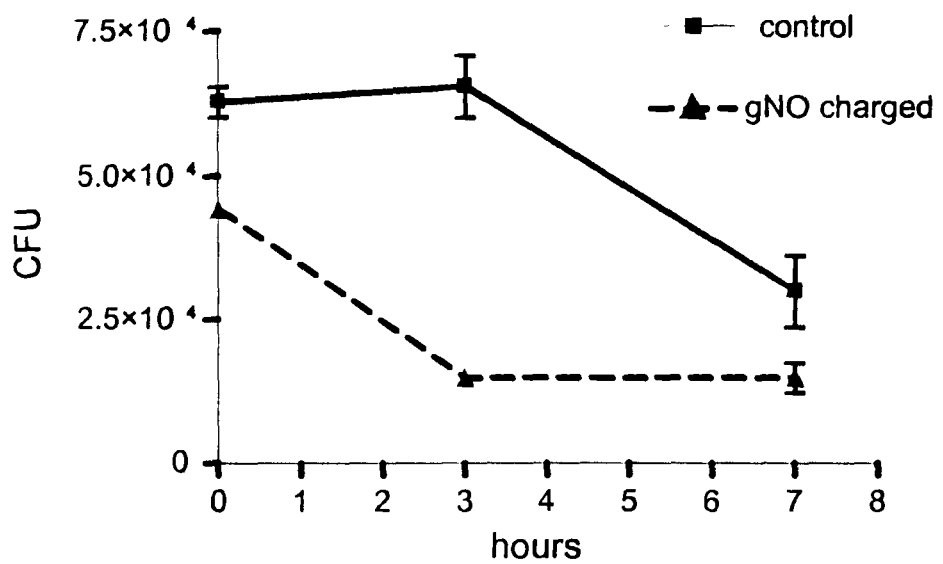
FIG. 1(a) is a chart showing the effects of gNO released from gNO-charged vent tubes on the proliferation of Streptococcus pyogenes.
Figure 1B:
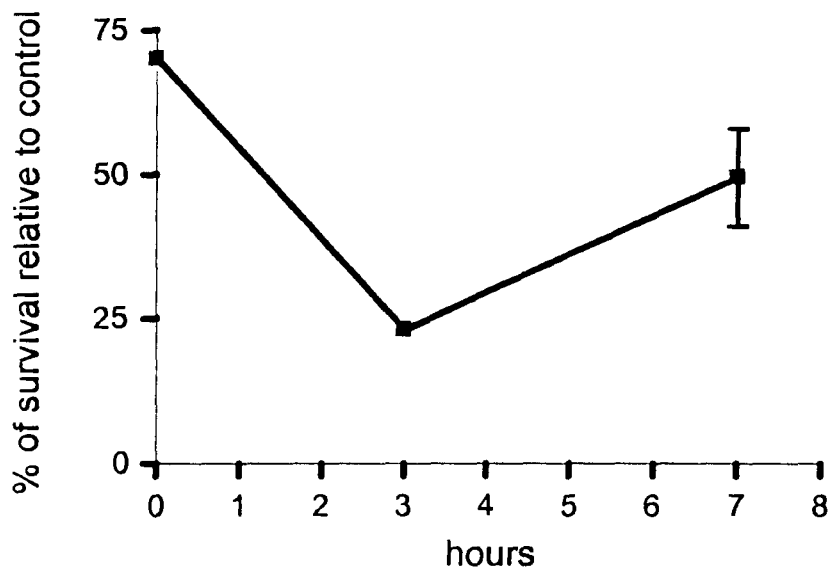
FIG. 1(b) is a chart showing the effects of released gNO on survival of S. pyogenes.
Figure 2A:
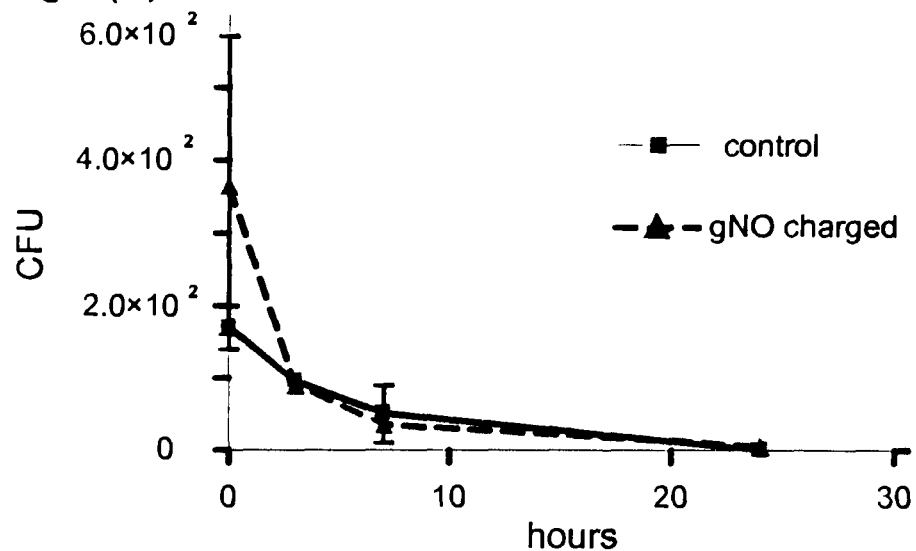
FIG. 2(a) is a chart showing the effects of gNO released from gNO-charged vent tubes on the proliferation of Streptococcus pneumonia.
Figure 2B:
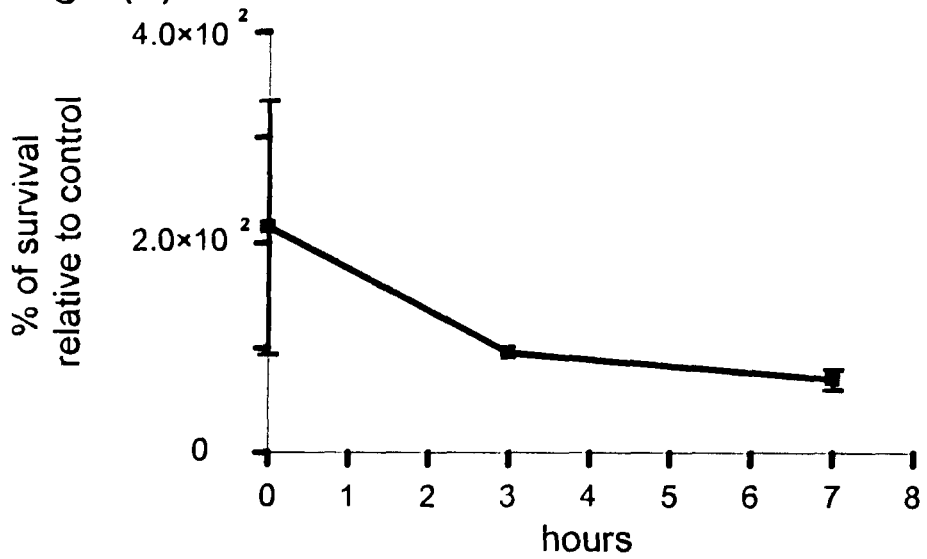
FIG. 2(b) is a chart showing the effects of released gNO on survival of S. pneumonia.
Figure 3A:
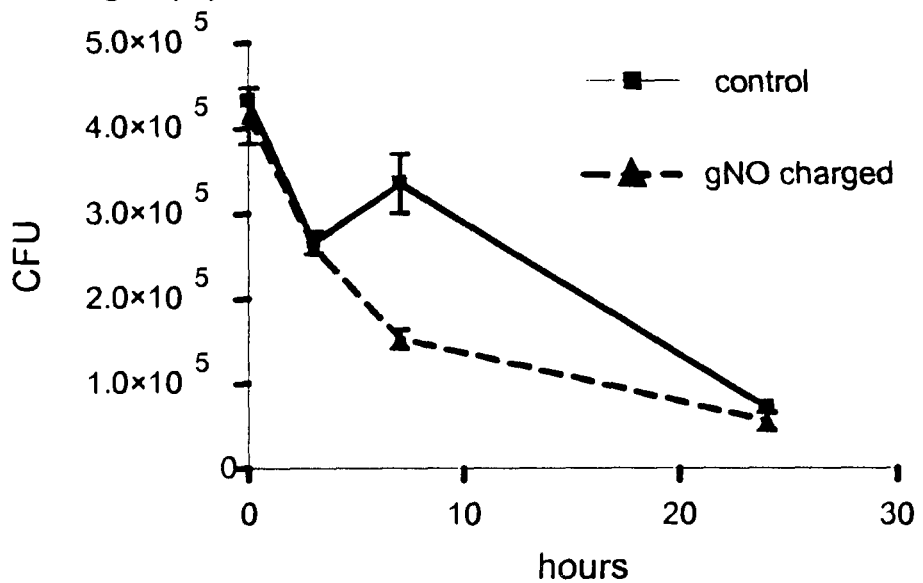
FIG. 3(a) is a chart showing the effects of gNO released from gNO-charged vent tubes on the proliferation of Moraxella catarrhalis.
Figure 3B:
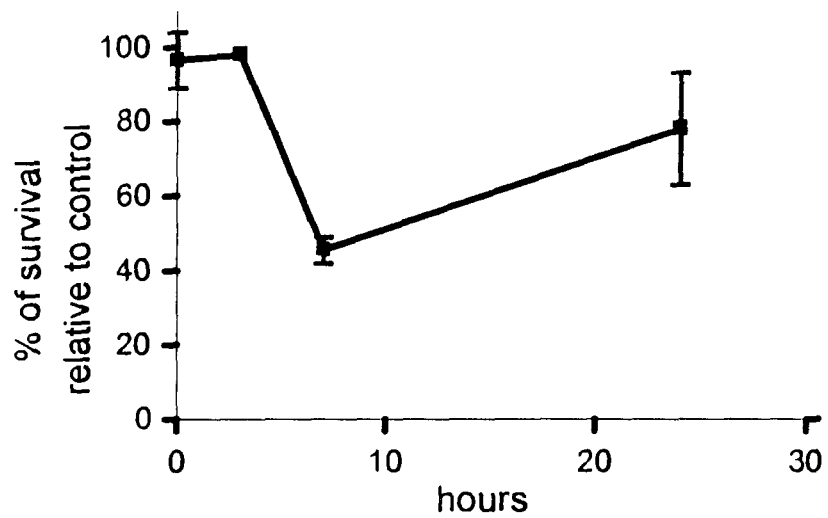
FIG. 3(b) is a chart showing the effects of released gNO on survival of M. catarrhalis.
Figure 4A:
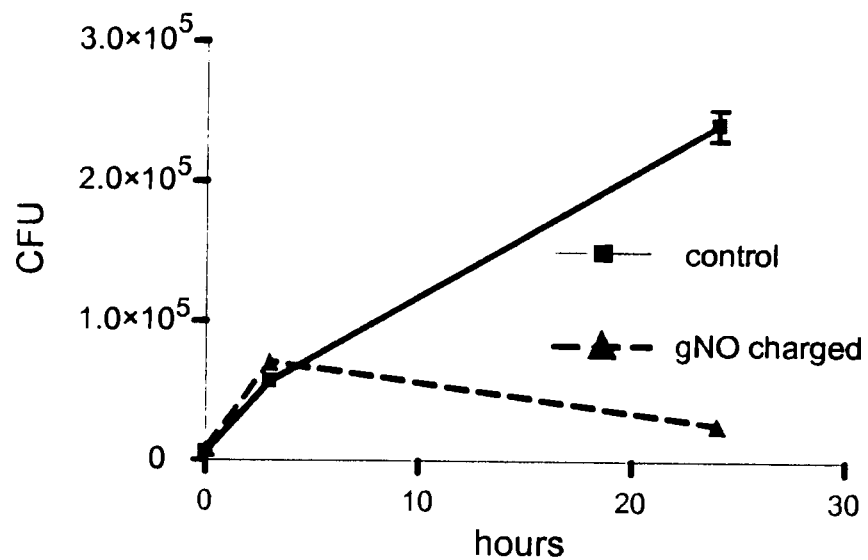
FIG. 4(a) is a chart showing the effects of gNO released from gNO-charged vent tubes on the proliferation of Haemophilus influenzae.
Figure 4B:
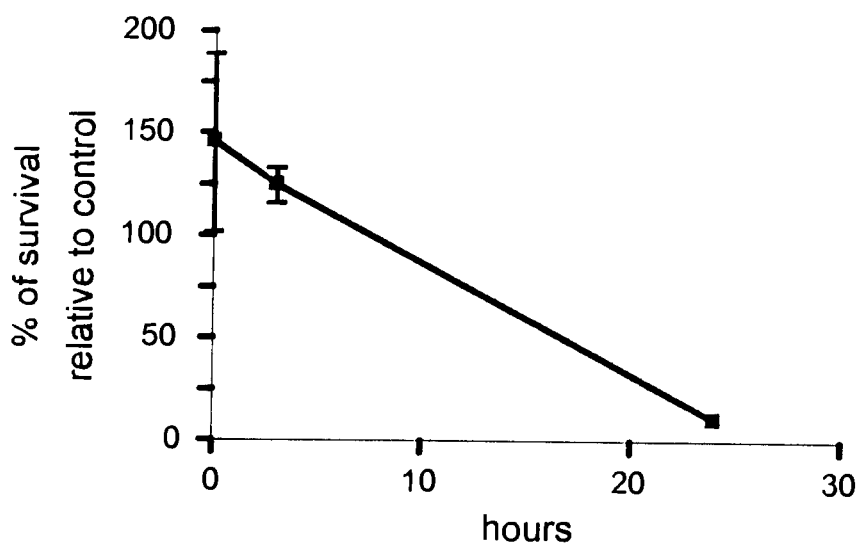
FIG. 4(b) is a chart showing the effects of released gNO on survival of H. influenzae.

Certain exemplary embodiments of the present invention are directed to antimicrobial conduit structures configured for long-term installation through the tympanic membranes into the inner ear cavities for the purpose of draining fluids therefrom. Such conduit structures are exemplified by tympanostomy tubes, myringotomy ventilation tubes and the like, and will be generally referred to from hereon in as "tympanostomy tubes". The antimicrobial tympanostomy tubes generally comprise materials that are controllably permeatable with gases selected for their antimicrobial properties.

The antimicrobial tympanostomy tubes are characterized by their biological compatibility with otologic tissue associated with the tympanic membrane and middle ear tissues, and generally comprise polymeric materials exemplified by resins which after forming and curing, are microporous and have the requisite high gas permeability properties needed to prepare the antimicrobial tympanostomy tubes. These resins are suitably characterized by an ability for infiltratably sequestering selected permeating antimicrobial gases, and then controllably releasing the antimicrobial gases over extended periods of time. Suitable resins are exemplified by curable silicones, polyvinyl acetates, thermoplastic elastomers, acrylonitrile-butadiene-styrene copolymer rubber, polyurethanes and the like. In certain embodiments, curable silicone resins are preferred for the manufacture of the antimicrobial tympostomy tubes due to their molecular structure which provides good flexibility both microscopically and macroscopically, and high gas permeability rates. Table 1 illustrates the gas permeability of silicone resins in comparison with other types of materials suitable for such tubular manufacture.

The geometries of the antimicrobial tympanostomy tubes are generally cylindrical and may simply comprise elongate hollow conduits having the same diameter extending from end to end, or alternatively may comprise elaborate configurations that may additionally include abrupt diameter changes and odd shaped flanges.

TABLE 1

Gas permeation through selected materials (cc/0.001 in/100.0 in$^2$/24 h at 22.8° C., 0% relative humidity, ASTM D-1434)*.

| Tubular material | Permeating gas | |
|---|---|---|
| | $O_2$ | $CO_2$ |
| Silicone | 50,000 | 300,000 |
| Urethanes | 200 | 3,000 |
| Epoxies | 5-10 | 8 |
| Fluorocarbons | 7-15 | 15-30 |
| Nylon | 2.6 | 4.7 |
| Polybutylene | 385 | 825 |
| Polycarbonate | 258 | 775 |
| Cellulose acetate | 23 | 105 |

*adapted from; (1) Packaging Encyclopedia 1988 Vol. 33 No. 5, pp. 54-55, and Machine Design, May 25, 1967, p. 192.

Gaseous nitric oxide (gNO) is an intermediary compound produced during the normal functioning of numerous biochemical pathways in many biological systems including humans. gNO is known to those skilled in these arts as a key biological messenger signaling compound that plays key roles in many biological processes. Recent evidence (e.g., Ghaffari et al., 2005 Nitric Oxide 14: 21-29) suggests that gNO plays an important role in mammalian host defense against infection and regulates wound healing and angiogenesis. In particular, topical applications of exogenous gNO at 200 ppm for extended periods of time inhibited and prevented the growth of a wide range of microbial pathogens *Staphylococcus aureus, Escherichia coli*, Group B *Streptococcus, Pseudomonas aeruginosa*, and *Candida albicans*, without any cytotoxic effects on cultured human dermal fibroblasts. Furthermore, McMullin et al. (2005, Respir. Care 5:1451-1456) demonstrated that exogenous gNO at a concentration of 200 ppm could clear nosocomial pneumonia caused by microbial pathogens such as *S. aureus* and *P. aeruginosa*, in about 6 hours. Accordingly, gNO is a particularly suitable antimicrobial gas for saturatingly permeating tympanostomy tubes comprising gas-permeable polymeric materials.

The antimicrobial typanostomy tubes described herein may be produced by first casting a desired tubular configuration with a selected suitable resin using conventional methods known to those skilled in these arts. It is suitable to process the tubes into their final configuration and finish after which, the tubes are placed into a sealable chamber. The chamber is then saturated with a selected antimicrobial gas, exemplified by gNO, for a selected period of time suitable for infiltratingly saturating the tympanostomy tubes whereby the gas is sequestered into and within the resin structure comprising the tubes thereby by providing antimicrobial properties to the tympanostomy tubes. Excess gNO is then evacuated from the chamber after which, the gNO-loaded tympanostomy tubes are removed and individually packaged into gas-impermable containers. In certain embodiments, the chamber may be infiltrated with a semi-porous sealing gaseous material configured to at least partially cross-link with the outer surfaces antimicrobial tympanostomy tubes thereby enabling a further extension of time duration for release of the sequestered gas about the antimicrobial tympanostomy tubes. The chamber may be controllably infiltrated with the semi-porous sealing gaseous material concurrently with evacuation of the antimicrobial gas from the chamber or alternatively, the antimicrobial gas may be completely evacuated from the chamber after which, the semi-porous sealing gaseous material may be infiltrated into the chamber. Excess semi-porous sealing gaseous material is then evacuated from the chamber after which, the gNO-loaded tympanostomy tubes are removed and individually packaged into gas-impermable containers.

In certain embodiments, gNO-sequestering chelating agents may be incorporated into a suitable selected resin material prior to forming tympanostomy tubes. Suitable gNO-sequestering chelating agents are exemplified by sodium nitrite, nitrosothiols, dipyridoxyl chelating agents, L-arginine, organic nitrates, organic nitrites, thionitrates, thionitrites, N-oxo-N-nitrosamines, N-nitrosamines, sydnonimines, 2-hydroxyimino-5-nitroalkenamides, diazenium diolates, oxatriazolium compounds, oximes, syndomines, molsidomine and derivatives thereof, pirsidomine, furoxanes, nitrosonium salts, and the like, and combinations thereof. A suitable amount of a selected gNO-sequestering chelating agent is placed into a sealable chamber which is then saturated with gNO. A suitable amount of the gNO-loaded chelating agent is then thoroughly intermixed and commingled with a selected resin material after which, the resin material is processed into tympanostomy tubes using methods known to those skilled in these arts. The tympanostomy tubes comprising interspersed therethrough gNO-loaded chelating agent, are then sealably packaged into gas-impermeable containers.

In certain embodiments, an antimicrobial gas-releasing coating may be provided onto the outer surfaces, and optionally on to the inner surfaces, of NO gas-permeated tympanostomy tubes. For example, NO gas-releasing coatings can be provided by applying to the NO gas-permeated tympanostomy tubes, a composition comprising a $N_2O_2^-$ functional group that will bind to the cured resin material comprising the tympanostomy tubes. Suitable exemplary compounds comprising $N_2O_2^-$ functional groups are disclosed in U.S. Pat. No. 5,525,357. Other suitable exemplary coating compositions for providing NO gas-releasing coatings onto NO gas-permeated tympanostomy tubes include among others, NO-releasing intramolecular salts known as zwitterions having the general formula $2RN[N(O)NO^-(CH_2),NH_2^+R'$, and S-nitrosothiols.

The antimicrobial gas-permeated tympanostomy tubes described herein can be surgically implanted using well-known procedures, through a patient's tympanic membrane such that one end of the tympanostomy tube extends into the patient's middle ear cavity while the other end of the tube extends through the tympanic membrane into the outer ear cavity. The antimicrobial gas sequestered within the resin material comprising the implanted tympanostomy tube will slowly diffuse from and about the tube thereby alleviating and/or preventing post-operative microbial infections normally associated with these types of tubes and without adverse toxicology reactions exemplified by irritation and inflammation, of otologic tissues. Contact with moisture will expedite the release of gNO sequestered within and coated onto the antimicrobial tympanostomy tubes. Furthermore, provision of NO gas-releasing coatings on the outer surfaces of the tubes, and optionally on their inner surfaces, will inhibit and prevent the formation of biofilms thereon.

EXAMPLES

Example 1

A plurality of vent tubes comprising a polytetrafluoroethylene (PTFE) substrate (1.25 mm Sheehy collar buttons, catalog number 23-40300; Inovotec International Inc., Jacksonville, Fla., USA) were placed into gas-ventable Petri dishes. A suitable cather was used to connect the Petri dishes to a manifold connected to a cylinder containing gNO manufactured by Airgas (Chicago Ill., USA). The manifold was provided with a gas flow controller adjusted to deliver 22,000 ppm of gNO to each Petri dish at a flow rate of 30 cc $min^{-1}$ for a period of 22 h. After the gNO-charging process was completed, the gNO-charged PTFE vent tubes were stored in gas-impermeable containers. All handling of the vent tubes after the gNO-charging process was completed, was done using aseptic techniques.

Stock cultures of *Streptococcus pyogenes* (ATCC#51878), *Streptococcus pneumonia* (ATCC#10015), *Moraxella catarrhalis* (ATCC#25240), and *Haemophilus influenzae* (ATCC#35540) were maintained on nutrient agar. Broth cultures of each microorganism were prepared by inoculating a test tube containing 10 mL of Brain Heart infusion broth with a colony picked from a stock culture plate. The inoculated test tubes were cultured for 12 h to 18 h at 37° C. in an incubater provided with an atmosphere containing about 5% $CO_2$. The cultures were then diluted with fresh Brain Heart Infusion broth to an $OD_{600}$ reading of 0.5. Each broth culture thus prepared contained $10^7$ to $10^8$ colony-forming units (CFU) mL$^{-1}$. All handling of the microbial cultures was done using aseptic techniques.

All wells in a 24-well plate received 1 mL of broth culture of a selected microorganism prepared as described above. Each of 12 wells received 1 gNO-charged PTFE vent tube prepared as described above. Each of the remaining 12 wells received 1 sterile PTFE vent tube as supplied by the manufacturer. The tubes were incubated in the broth cultures contained in the 24-well plates for about 1 min after which, each tube was removed from its broth culture and transferred to a quadrant in a quadrant Petri dish. The quadrant Petri dishes were maintained for 7 h at 37° C. in an incubater provided with an atmosphere containing about 5% $CO_2$. Individual tubes were removed from the quadrant Petri dishes after 3 h and 7 h of incubation, and were each placed into a microtubes containing 30 μL of sterile phosphate-buffered saline (PBS) and vortexed. The PBS was then pipetted onto a nutrient agar plate and spread across the agar surface. The inoculated plates were then incubated for 24 h at 37° C. in an incubater provided with an atmosphere containing about 5% $CO_2$ after which, the plates were removed and the numbers of CFU units appearing thereon were quantified. The results are shown in FIGS. 1-4. The data show that exposure of *S. pyogenes* (FIGS. 1(*a*) and 1(*b*)), *S. pneumonia* (FIGS. 2(*a*) and 2(*b*)), *M. catarrhalis* (FIGS. 3(*a*) and 3(*b*)), and *H. influenzae* (FIGS. 4(*a*) and 4(*b*)) to gNO-charged vent tubes reduced the proliferation of each of the microbial species tested.

Example 2

A plurality of vent tubes comprising a PTFE substrate (Armstrong Beveled vent tube Grommet-type 1.14 mm I.D Fluorplastic, from Gyrus ACMI, catalog number 140242; Inovotec International Inc., Jacksonville, Fla., USA) were placed into gas-ventable Petri dishes. A suitable cather was used to connect the Petri dishes to a manifold connected to a cylinder containing gNO manufactured by Airgas (Chicago Ill., USA). The manifold was provided with a gas flow controller adjusted to deliver 22,000 ppm of gNO to each Petri dish at a flow rate of 30 cc min$^{-1}$ for a period of 22 h. After the gNO-charging process was completed, the gNO-charged PTFE vent tubes were stored in gas-impermeable containers. All handling of the vent tubes after the gNO-charging process was completed, was done using aseptic techniques.

A stock culture of methicillin-resistant *Staphylococcus aureus* (MRSA; ATCC#700698), was maintained on nutrient agar. MSRA is a *S. aureus* strain that is known to be resistant to a number of broad-spectrum antibiotics commonly used to treat it. MRSA broth cultures were prepared by inoculating a plurality of test tubes containing 10 mL of Brain Heart Infusion broth with a colony picked from a stock culture plate. The inoculated test tubes were cultured for 12 h to 18 h at 37° C. in an incubater provided with an atmosphere containing about 5% $CO_2$. The cultures were then diluted with fresh Brain Heart Infusion broth to an $OD_{600}$ reading of 0.5. Each broth culture thus prepared contained about $10^5$ CFU mL$^{-1}$. All handling of the microbial cultures was done using aseptic techniques.

Figure 5A:
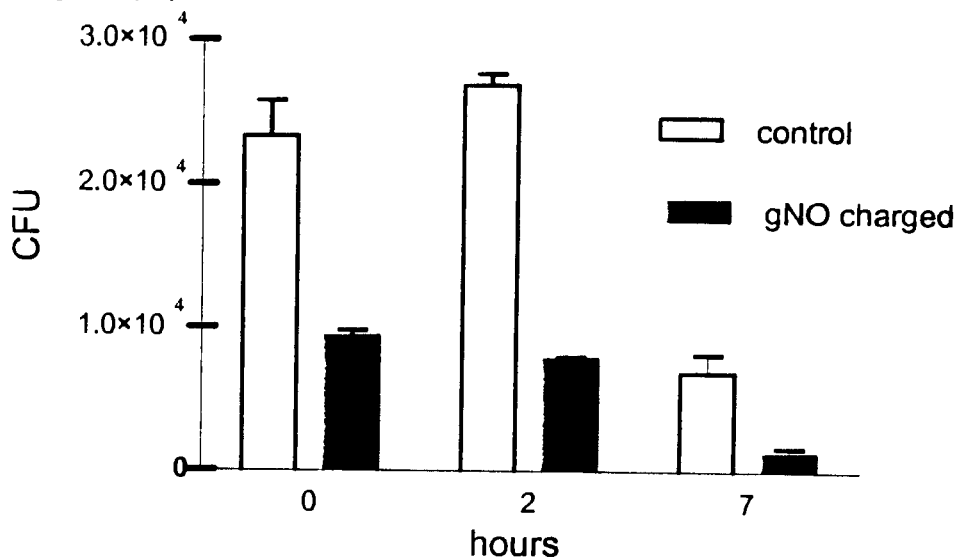
FIG. 5(a) is a chart showing the effects of gNO released from gNO-charged vent tubes on the proliferation of methicillin-resistant Staphylococcus aureus.
Figure 5B:
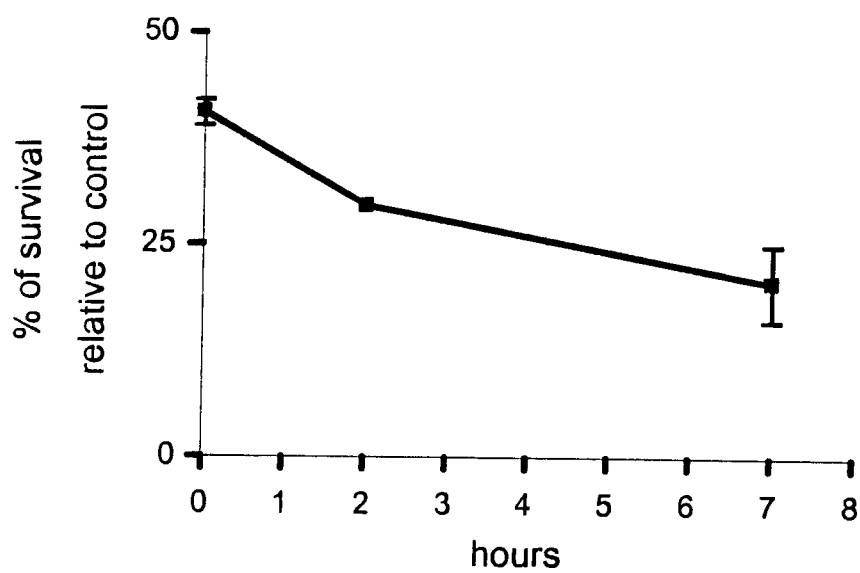
FIG. 5(b) is a chart showing the effects of released gNO on survival of S. aureus.

All wells in a 24-well plate received 1 mL of a MSRA broth culture prepared as described above. Each of 12 wells received 1 gNO-charged PTFE vent tube prepared as described above. Each of the remaining 12 wells received 1 sterile PTFE vent tube as supplied by the manufacturer. The tubes were incubated in the broth cultures contained in the 24-well plates for about 1 min after which, each tube was removed from its broth culture and transferred to a quadrant in a quadrant Petri dish. The quadrant Petri dishes were maintained for 7 h at 37° C. in an incubater provided with an atmosphere containing about 5% $CO_2$. Individual tubes were removed from the quadrant Petri dishes after 3 h and 7 h of incubation, and were each placed into a microtubes containing 30 μL of sterile phosphate-buffered saline (PBS) and vortexed. The PBS was then pipetted onto a nutrient agar plate and spread across the agar surface. The inoculated plates were then incubated for 24 h at 37° C. in an incubater provided with an atmosphere containing about 5% $CO_2$ after which, the plates were removed and the numbers of CFU units appearing thereon were quantified. The results are shown in FIG. The data show that exposure of methicillin-resistant *Staphylococcus aureus* (FIGS. 5(*a*) and 5(*b*)) to gNO-charged vent tubes reduced the proliferation of this microbial species.

Example 3

A first plurality of vent tubes comprising a silicon substrate (T-Tube, Silicon Myringotomy Tube, 23-50600; Invotec International Inc., Jacksonville, Fla., US) and a second plurality of vent tubes a PTFE substrate (Sheehy Collar Button, Fluoroplastic Myringotomy Tube, 23-40300; Inovotec International Inc., Jacksonville, Fla., USA) were placed into gas-ventable Petri dishes. A suitable cather was used to connect the Petri dishes to a manifold connected to a cylinder containing gNO manufactured by Airgas (Chicago Ill., USA). The manifold was provided with a gas flow controller adjusted to deliver 22,000 ppm of gNO to each Petri dish at a flow rate of 30 cc min$^{-1}$ for a period of 22 h. After the gNO-charging process was completed, the gNO-charged silicon vent tubes and PTFE vent tubes were stored in gas-impermeable containers. All handling of the vent tubes after the gNO-charging process was completed, was done using aseptic techniques.

A stock culture of a *Staphylococcus aureus* (ATCC#25923), was maintained on nutrient agar. *S. aureus* broth cultures were prepared by inoculating a plurality of test tubes containing 10 mL of Brain Heart Infusion broth with a colony picked from a stock culture plate. The inoculated test tubes were cultured for 12 h to 18 h at 37° C. in an incubater provided with an atmosphere containing about 5% $CO_2$. The cultures were then diluted with fresh Brain Heart Infusion broth to an $OD_{600}$ reading of 0.5. Each broth culture thus prepared contained about $10^5$ CFU mL$^{-1}$. All handling of the microbial cultures was done using aseptic techniques.

Figure 6:
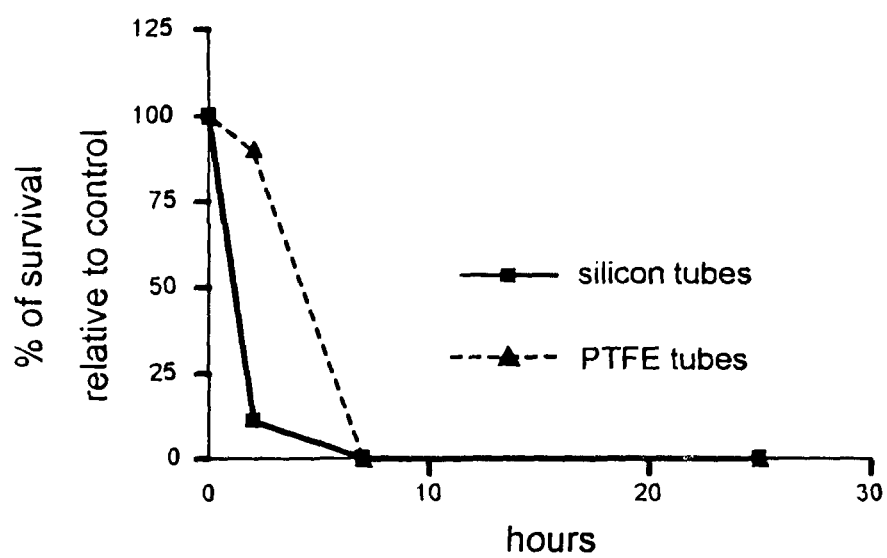
FIG. 6 is a chart showing the effects of gNO released from gNO-charged silicon vent tubes and gNO-charged polytetrafluoroethylene vent tubes on the proliferation of Staphylococcus aureus.
Figure 7:
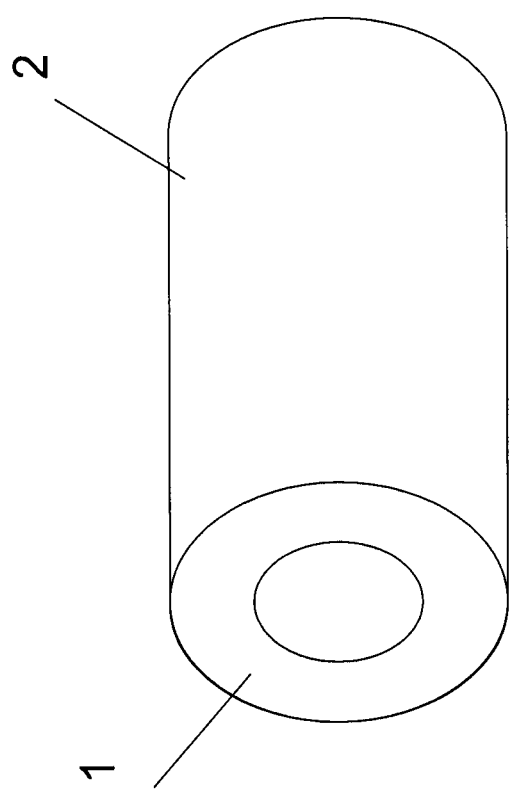
FIG. 7 provides a schematic illustration of an embodiment of the presently described conduit, wherein a hollow tube 1 can be coated on the outer surface 2 with a coating comprising antimicrobial gas-releasing coating.

All wells in a 24-well plate received 1 mL of a *S. aureus* broth culture prepared as described above. Each of 12 wells received 1 gNO-charged PTFE vent tube prepared as described above. Each of the remaining 12 wells received 1 sterile PTFE vent tube as supplied by the manufacturer. The tubes were incubated in the broth cultures contained in the 24-well plates for about 1 min after which, each tube was removed from its broth culture and transferred to a quadrant in a quadrant Petri dish. The quadrant Petri dishes were maintained for 7 h at 37° C. in an incubater provided with an atmosphere containing about 5% $CO_2$. Individual tubes were removed from the quadrant Petri dishes after 3 h and 7 h of incubation, and were each placed into a microtubes containing 30 μL of sterile phosphate-buffered saline (PBS) and vortexed. The PBS was then pipetted onto a nutrient agar plate and spread across the agar surface. The inoculated plates were then incubated for 24 h at 37° C. in an incubater provided with an atmosphere containing about 5% $CO_2$ after which, the plates were removed and the numbers of CFU units appearing thereon were quantified. The results are shown in FIG. The data show that exposure of *S. aureus* ATCC#25923 to gNO-charged vent tubes reduced the proliferation of this microbial species on silicon-based vent tubes and on PTFE vent tubes (FIG. 6).

While this invention has been described with respect to the exemplary embodiments, it is to be understood that various alterations and modifications can be made to the configurations and shapes of the antimicrobial tympanostomy tubes, and to methods for saturatingly infiltrating the tubes with a selected antimicrobial gas within the scope of this invention.

Further, the foregoing is merely intended to illustrate various embodiments of the present invention. The specific modifications or characteristics discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

What is claimed is:

1. An antimicrobial gas-releasing conduit comprising an elongate hollow tube that is sufficiently flexible to be implantable within a patient, which tube comprises a gas-permeable cured resin material having a porous microstructure, wherein the porous microstructure of said gas-permeable cured resin material is saturated throughout with antimicrobial gaseous nitric oxide and is devoid of an antimicrobial gas-releasing composition, the conduit being configured such that the gaseous nitric oxide is releasably sequestered in said porous microstructure and thus is released, after implantation of the conduit within a patient, so as to diffuse about the tube and provide antimicrobial gas to the surrounding tissue.

2. The antimicrobial gas-releasing conduit of claim 1, wherein said gas-permeable cured resin material is selected from the group consisting of curable silicones, polyvinyl acetates, acrylonitrile-butadiene-styrene copolymer rubber and polyurethanes.

3. The antimicrobial gas-releasing conduit of claim 1, wherein said elongate hollow tube, that is sufficiently flexible to be implantable within a patient, is an ear-draining tube.

4. The antimicrobial gas-releasing conduit of claim 1, wherein said elongate hollow tube, that is sufficiently flexible to be implantable within a patient, is a tympanostomy tube.

5. The antimicrobial gas-releasing conduit of claim 1, wherein said elongate hollow tube, that is sufficiently flexible to be implantable within a patient, is a myringotomy tube.

6. A method for treating otitis media in a patient comprising implanting the antimicrobial gas-releasing conduit of claim 1 in a patient's tympanic membrane.

7. The method of claim 6, wherein said antimicrobial gas-releasing conduit is a tympanostomy tube.

8. The method of claim 6, wherein said antimicrobial gas-releasing conduit is a myringotomy tube.

* * * * *